Figure 1:
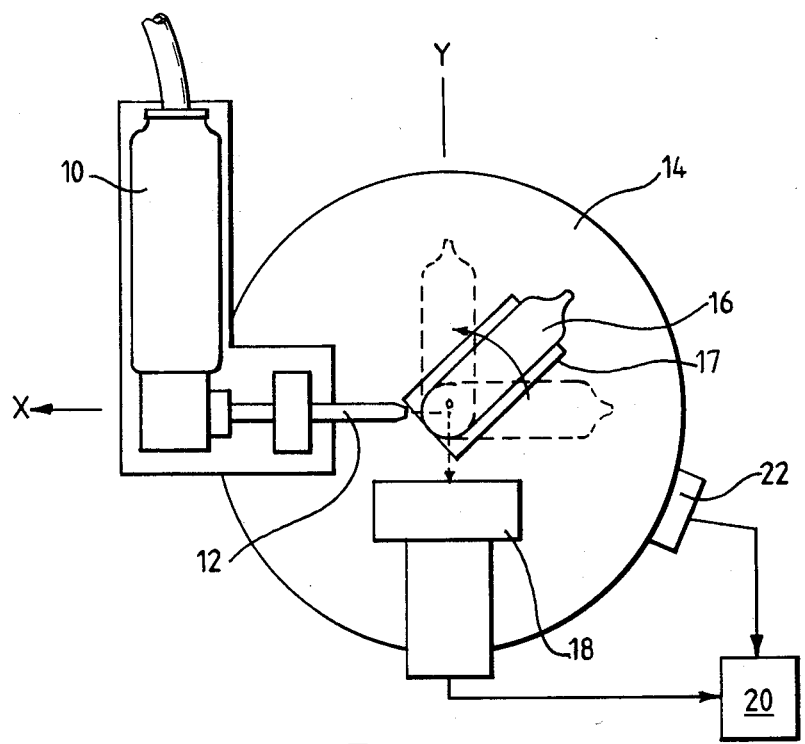

United States Patent [19]

Howe et al.

[11] Patent Number: 4,788,702
[45] Date of Patent: Nov. 29, 1988

[54] ORIENTATION OF CRYSTALS

[76] Inventors: Stephen Howe, 13D Venice Court, 41 Conduit Rd., Hong Kong, Hong Kong; Donald Rogers, 11 Salvington Crescent, Bexhill on Sea, United Kingdom

[21] Appl. No.: 894,655

[22] Filed: Aug. 8, 1986

[30] Foreign Application Priority Data

Mar. 26, 1986 [GB] United Kingdom ................. 8607482

[51] Int. Cl.⁴ .......................................... G01N 23/207
[52] U.S. Cl. ....................................... 378/73; 378/71; 378/79
[58] Field of Search ....................... 378/73, 71, 76, 79, 378/86, 49

[56] References Cited

U.S. PATENT DOCUMENTS 3,784,816  1/1974  Abrahamsson ....................... 378/73
3,870,880  3/1975  Merigoux et al. ..................... 378/73

Primary Examiner—Carolyn E. Fields
Assistant Examiner—David P. Porta
Attorney, Agent, or Firm—Kane, Dalsimer, Kurucz, Levy, Eisele & Richard

[57] ABSTRACT

The invention comprises apparatus for determining the orientation of the crystallographic axes of a single crystal. The crystal is rotated on a turntable while an X-ray beam containing characteristic radiation is directed onto it. A stationary position-sensitive detector, preferably positioned at right angles to the beam detects Bragg reflections from the crystal, and computing means responsive to the signals from the detector, and signals representing the angular position of the turntable determines the crystal orientation.

4 Claims, 1 Drawing Sheet

ORIENTATION OF CRYSTALS

This invention relates to the determination of the orientation of the crystallographic axes of a single-crystal such as may be required preparatory to cutting a boule or polishing a wafer. It is applicable in both laboratory and industrial contexts and is especially relevant to the production of microchips from boules.

The rate of deposition of epitaxial layers (or the depth of penetration of ion implantation) during the subsequent formation of integrated circuits on the surface of a wafer is markedly dependent on the degree of misalignment between the growth face and the crystallographic planes in the substrate, and the electronic switching speeds achievable is the finished product depend on the thickness of such deposits. It has become important, therefore, especially in the batch production of microprocessors, to control the orientation of the prepared surface of the wafers, and to make any deliberate misalignments that are desirable in the interests of high switching speeds as reproducible as possible: and that requires precise angular measurements. Sufficient accuracy is achievable with some of the current techniques but always at a high price in time.

Current practice is to affix the boule to a base plate with epoxy resin as a means of holding it while cutting, to determine the errors in the orientation of its crystallographic axes by means of an X-ray diffraction technique, and having transferred the specimen on its base plate to the cutter/polisher, to make angular corrections on that instrument to ensure that resulting surface has the desired orientation. Such methods usually employ monochromatic (characteristic) radiations and involve measurement of the Bragg angle of one diffracted beam at a time. Where comparison of two such beams is made they are profiled separately and, when accuracy is needed, this is a relatively slow process that calls for a stabilised X-ray source which is expensive. It also necessitates duplication of the angular correction facilities on the cutter/polisher.

Conventional techniques depend upon the preliminary step of predicting where a given Bragg reflexion is likely to occur. The specimen is first oriented, for example, by photographic techniques so that the selected Bragg reflexion can be identified and measured with accuracy. With a single-crystal diffractometer having a small-aperture detector, this involves adjusting the position of the detector and the orientation of the crystal relative to three mutually perpendicular axes, until the reflexion passes through the detector collimator. Having identified any symmetry that may be apparent and knowing the disposition of particular Bragg reflexions relative to a given datum, it is possible to compute the orientation of the crystallographic axes relative to tha datum.

One object of the invention is to enable high precision setting to be achieved routinely and much more rapidly than with conventional techniques, and without the need to duplicate correction facilities. According to the present invention, we now propose ascertaining the orientation of a crystal specimen by irradiating the crystal specimen with a beam of X-rays (OX) on an X-ray diffractometer, rotating the specimen about an axis (OZ) perpendicular to a plane (XOY) containing the beam so as to cause reflected beams to impinge upon a position sensitive detector operable to generate co-ordinate data corresponding to all Bragg reflexions received by the detector, noting for each Bragg reflexion the co-ordinate data and data representing the angular position ($\omega$) of the specimen relative to its initial position and computing from that data the orientation matrix or its equivalent.

If the X-ray radiation is monochromatic then only the reflexions of interest impinge (flash) momentarily on the position sensitive detector but it will be understood that the invention is applicable also to the use of white radiation. Most X-ray diffraction tubes will, in addition to white radiation generate intense peak energy at a wavelength characteristic of the target material in the tube when operated above the critical voltage. In such cases the reflexions will pass over the detector which can be adapted to respond only when the brightness of the reflexion exceeds a predetermined threshold (i.e. when the reflexion "flashes").

In general the invention is suitable for ascertaining the orientation of all crystal structures although the complexity of the necessary computation increases with decreasing symmetry of the crystal structure.

The position sensitive detector may be of any suitable kind. One suitable detector is based on a two-dimensional mesh of wires which register the number of photons landing near the cross-over of two wires. Another is a solid state photon counter and another may comprise a flourescent screen, an image intensifier, a vidicon and an analogue to digital converter all connected to a processor.

The co-ordinate data generated by the position-sensitive detector may be in any convenient co-ordinate frame. In the preferred embodiment the detector axis is set at an angle of 90° to the X-ray beam in the equatorial plane such that the flat-screen thereof lies parallel to the XOZ plane.

For each observed reflexion, the data (X, Z, $\omega$) is used to compute the magnitude and direction cosine of the relevant reciprocal lattice vector (rlv) at the moment of flashing. Next, the angular position data ($\omega$) is used to convert to cartesian co-ordinates so as to refer all reflexions to a common orientation which is to be expressed as an orientation matrix referred to the diffractometer axes (OXYZ), the XYZ co-ordinates then enabling the form {hkl} of the reflexions to be identified.

This is a relatively simple computation for a cubic crystal but less so for tetragonal, hexagonal, or trigonal structures and becomes increasingly difficult due to greater ambiguity, as the symmetry of the crystal structure decreases.

The direction cosines for the different reflexions are then used to compute the angle between the reciprocal lattice vectors of the observed reflexions so that it is possible to identify which members of each form could give such angles. The possible reciprocal lattice vector sets are then correlated using the least number to produce an initial approximation to the orientation matrix.

A least-squares calculation is then performed by the computer using the initial approximation together with the observed data, to improve the accuracy of the matrix elements.

The orientation matrix may provide sufficient information for the required purpose but in the context of a process, for example, for the production of wafers, the computer preferably then calculates the adjustments, with reference to a convenient datum which in practice is matched between (e.g.) the diffractometer and the cutter or polisher (typically the axis of the X-ray beam and the axis of rotation of the cutter), that need to be applied in order to set the orientation of the crystallographic axis of the crystal specimen. This computation may, if required, account for any deliberate mis-setting that is required for the reasons stated above.

It will be understood that no provision is made for adjustments to be made on the diffractometer, the necessary adjustments obtained in accordance with the invention and stored in the computer being available for display and manual setting or for automatic setting of the crystal specimen in the cutter.

Our co-pending application PCT/GP No. 84/00324 discloses supports or fixtures suitable for mounting a specimen in the diffractometer and subsequent transfer to a cutter or polisher, so as to preserve the datum reference of the orientation matrix.

Figure 2:
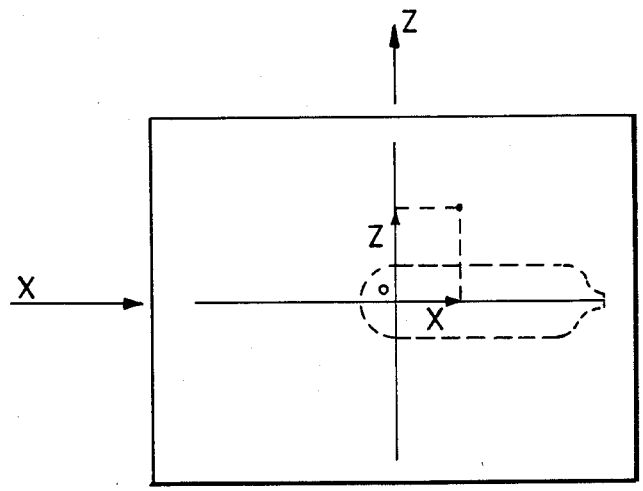

One embodiment of the invention will now be described by way of example with reference to the accompanying drawings in which:

FIG. 1 is a plan view of a diffractometer for determining the orientation of a crystal specimen; and FIG. 2 is a diagram illustrating the screen of a position sensitive detector forming part of the diffractometer of FIG. 1 and indicating the co-ordinate data generated.

The diffractometer shown in FIG. 1 comprises an X-ray diffraction tube 10 and a collimator 12 producing a narrrow parallel X-ray beam (OX) of circular cross-section and intersecting the axis (OZ) of rotation of a turntable 14 on which a crystal specimen 16 (in this case a boule) is mounted. The specimen is preferably mounted in a holder or fixture 17 enabling reproducible transfer to (e.g.) a cutter. It may, for example, be a 3-legged (hole, slot, plane) base plate or other holder or fixture such as described in our copending Application PCT/GB No. 84/00324.

The specimen is positioned such that the point of impingement of the incident X-ray beam thereon coincides with the axis of rotation of the table 14 (i.e. the origin of the diffractometer axes).

A flat wide aperture position-sensitive detector 18 is mounted adjacent to the table on a support arm arranged for angular movement relative to the table about the axis OZ. It is set, with its axis preferably at or near 90° to the X-ray beam (i.e. at or near (OY)). The detector 18 is coupled directly to a computer 20, which controls data capture from the detector and is also connected to means, 22, for measuring angular displacement ($\omega$) of the turntable about OZ.

No adjustments are provided for altering the orientation of the specimen (boule) relative to the diffractometer table. The object is to determine the corresponding orientation matrix which defines the oreintation of the boule relative to the diffractometer and then to use this matrix to apply corrections when the boule is transferred to the cutter.

The table is rotated steadily in a single scan over as large a range of angle $\omega$ as circumstances allow—preferably between ca. 45 and 120 deg. During this scan Bragg reflexions flash out momentarily, each over a brief range of $\omega$ values. For those that fall on the detector, the computer records the co-ordinates (X,Z) of the weighted C.G. of the detector area illuminated, together with the weighted C.G. of the corresponding $\omega$ values.

This give a considerable number (typically 12 to 30) sets of X, Z, $\omega$—many more than are provided in comparable circumstances by Laue techniques or are needed to identify the orientation of the specimen relative to the diffractometer. The surplus data are used in a least-squares calculation to improve the accuracy of the elements of the orientation matrix, and to derive from the covariant matrix estimates of the precision of its elements.

the overall process is expected to take from a few seconds to a maximum of 1–2 minutes: the time depends on the computer used and how it handles the two stages of data capture and data reduction.

The angular accuracy is considerably better than can be got from the Laue photograph technique which is pretty fast but relatively inexpensive—it needs merely a photograph and a free-standing computer. Back-reflexion photographs are normally used for all large X-ray opaque specimens but that geometry precludes the use of a Polaroid camera. For the materials and the radiations envisaged here there will only be a limited number of spots (up to ca 6) on a typical Laue photograph. The co-ordinates of each spot are measured and typed into the computer, but it can only calculate the direction cosines of the normals to each set of reflecting planes: their d-spacings and indices are not directly deducible. The computer then has to calculate all possible angles between these normals and compare them with those calculated from literature values. Such a program has been described for back-reflexion geometry by Christenson, Huang and Block (Met. Trans. 1971, 2, 1367–1370; 2, 2295–6), the disclosure of which is hereby incorporated by reference, who report that the computer took about 20 sec. to process the data.

The precision attainable is ca. 0.3 deg. at best. The process is not automatic: it requires human intervention.

In accordance with the present invention, the computation based upon the observed co-ordinate (X, Z) and angular position ($\omega$) data is as follows:

1. Convert the measured co-ordinates X(i) & Z(i), to X'(i) & Z'(i) by dividing each by DD, the distance from crystal to detector.

2. From X'(i), Z'(i) evaluate the co-ordinates of the reciprocal point that is in the reflecting position, i.e., on the surface of the Ewald (reflecting) sphere.

3. Use the rotation matrix R(z) to rotate the coordinates into the position they had when $\omega$ was zero. This ensures that all sets of co-ordinates x, y, z for the reciprocal-lattice points in use are referred to a common orientation irrespective of their position when they reflected.

4. The length of the vector from the origin of reciprocal space to each of these points gives the corresponding interplanar spacing (d) and therefore the value of the integer $N(ii) = h(i)^2 + k(i)^2 + l(i)^2$. Because of experimental errors the calculated values of N(ii) will not be exact integers, but the exact integral value should not be in doubt: the closeness will be an indicator of experimental precision. N(ii) indicates that the reflexion is of the form {hkl}, i.e. any one of the symmetry-related reflexions obtained by permuting h, k, l, and their negatives in any order. For crystal class m3m to which most of the materials of interest belong a general reflexion hkl (hkl all diferent and non-zero) has 48 symmetrical equivalents; hhl or hkO have 24; hhO has 12; hhh has 8 and hOO has 6.

5. If we could record three general reflexions these would suffice to determine the orientation of the reciprocal lattice and thus of the boule, but for germanium and copper K-alpha radiation reflexions of the form {531} are the only general reflexions that are likely to be observed, and in that case more than three reflexions are needed to reduce ambiguities. One can manage without having any general reflexions in the defining set, but it saves time to include as many of them as possible. For a few values of N(ii) there may be more than one corresponding set of hkl, e.g. 333 and 511: such reflexions may be kept in the list for later use, but cannot be used for identifying the orientation matrix.

6. Calculate all the angles between the first 4 or 5 reflexion normals in the list of observed reflexions and store them. It is an interesting fact that for cubic materials if one works with $N(ij)=SQR(N(ii)*N(jj))*\cos \phi ij$ instead of the angle $\phi ij$ between normals i and j, this too is an integer viz.

$$N(ij)=h(i)*h(j)+k(i)*k(j)+1(i)*1(j),$$

and again the closeness with which the value approximates an integer should leave no doubt about the integer intended and be a reassurance as to the accuracy of both the data and the calculations thus far.

7. Now take the first reflexion in the list in its standard form hkl and calculate the values of N(ij) for the angles between this one member of the first form and all members of the second form, and identify and store the results for those reflexions whose N (ij) match any in the observed list.

8. Repeat step 7 for the N(ij) between hkl and all members of the third form.

9. Now calculate the N(ij) for the angle between the short list of possible reflexions obtained in steps 7 and 8 and look for correspondences in the list of observed N(ij) obtained in step 6.

10. If this does not lead to a unique solution for the indices of the trio of reflexions, repeat step 7 for the reflexion hkl and all members of the fourth form and then repeat step 9, comparing them with the short list from step 9.

11. If this still does not lead to a unique solution, repeat step 10 for the fifth form in the list. (This step will only rarely be needed).

12. From these uniquely determined reflexions it is now possible to calculate the orientation matrix, and from this in turn to calculate the indices of every remaining reflexion in the observed list. Again, the calculations yield near-integers for the indices: the intended values should never be in doubt and the closeness is again a check on accuracy of the input data and of the calculations.

13. With this complete set of indices the program enters a least-squares recalculation of the orientation matrix elements.

14. There are several ways of estimating the overall precision: either from the "covariant" matrix—which gives the esd's of the elements, or by back-substitution into the observed equations to determine the errors in the observed reciprocal-lattice co-ordinates or the original measured angle.

All these calculations are automatic and need no human intervention.

What is claimed is:

1. A method of determining orientation of a single crystal relative to a predetermined set of orthogonal axes, comprising the steps of:
    directing an x-ray beam onto the crystal along one of said orthogonal axes, said x-ray beam including a peak of energy at a preselected wavelength;
    rotating relatively the crystal and said x-ray beam from an initial position to an angular position about a single axis perpendicular to a plane containing said x-ray beam so as to generate Bragg x-ray reflections;
    detecting said x-ray reflections by means of a two-dimensional position sensitive detector operable to generate coordinate data corresponding to said detected x-ray reflections that occur at said preselected wavelength and registering a first binary condition when said x-ray reflections at said preselected wavelength are below a predetermined intensity and a second binary condition when said x-ray reflections at said preselected wavelength are above said predetermined intensity;
    generating data representing said angular position of the crystal relative to said initial position; and
    computing orientation data for the crystal responsive to said binary conditions from said coordinate data and from said angular position data.

2. The method of claim 1 wherein said computing step is performed by a digital processor and said orientation data is an orientation matrix.

3. An x-ray diffractometer for determining the orientation of a single crystal relative to a predetermined set of orthogonal axes comprising:
    a crystal holder;
    a source of a beam of x-rays including a peak of energy at a preselected wavelength, said x-ray beam source being arranged to direct said beam of x-rays along one of said orthogonal axes;
    means for relatively rotating said crystal holder and said x-ray source from an initial position to an angular position about a single axis perpendicular to a plane containing said beam of x-rays so as to generate Bragg x-ray reflections;
    a position sensitive detector operable to detect said x-ray reflections from the crystal and to generate coordinate data corresponding to said detected x-ray reflections that occur at said preselected wavelength, said coordinate data comprises spatial dependent data of binary conditions wherein a first binary condition is registered when said x-ray reflections at said preselected wavelength are below a predetermined intensity and a second binary condition when said x-ray reflections at said preselected wavelength are above a predetermined intensity;
    an encoder providing data representative of the angular position of the crystal relative to said initial position; and
    means for computing orientation data for the crystal from said coordinate data and from said angular position data.

4. The diffractometer of claim 3 wherein said computing means is a digital processor and said orientation data is an orientation matrix.

* * * * *